United States Patent
Chen et al.

[11] Patent Number: 5,954,751
[45] Date of Patent: Sep. 21, 1999

[54] IMPLANTABLE DEFIBRILLATOR WITH STACKED TRANSISTOR SUBASSEMBLIES

[75] Inventors: Philip A. Chen, Angleton; Xiaohai T. He, Fort Worth; Scott A. Armstrong, Angleton; Thomas G. Sosebee, Lake Jackson, all of Tex.

[73] Assignee: Intermedics Inc., Angleton, Tex.

[21] Appl. No.: 09/007,665

[22] Filed: Jan. 15, 1998

[51] Int. Cl.$^6$ .................................................. A61N 1/39
[52] U.S. Cl. ................................ 607/5; 607/36; 257/684; 361/600; 361/767
[58] Field of Search ................................ 607/36, 2, 4, 5; 257/684, 784, 778; 361/600, 728, 736, 760, 767, 783; 428/901

[56] References Cited

U.S. PATENT DOCUMENTS

| | | | |
|---|---|---|---|
| 4,231,098 | 10/1980 | Tanimoto | 361/399 |
| 4,288,841 | 9/1981 | Gogal | 361/414 |
| 4,604,677 | 8/1986 | Suzuki et al. | 361/393 |
| 4,614,194 | 9/1986 | Jones et al. | 607/2 |
| 4,616,655 | 10/1986 | Weinberg et al. | 607/2 |
| 4,800,883 | 1/1989 | Winstrom | 128/419 |
| 5,370,669 | 12/1994 | Daglow et al. | 607/36 |
| 5,470,345 | 11/1995 | Hassler et al. | 607/36 |
| 5,855,995 | 1/1999 | Haq et al. | 607/5 |

*Primary Examiner*—William E. Kamm
*Assistant Examiner*—Kennedy J. Schaetzle
*Attorney, Agent, or Firm*—Trop, Pruner, Hu & Miles, P.C.

[57] ABSTRACT

An implantable cardiac defibrillator is provided. The implantable cardiac defibrillator includes a can, a storage cell for powering the defibrillator, and a circuit module disposed in the can for controlling the defibrillator. The circuit module has a first substrate, a first die coupled to the first substrate, a second die, and a second substrate coupled to and disposed between the first die and the second die. The second substrate has a first plurality of conductors to carry electrical signals to and from the first die and a second plurality of conductors to carry electrical signals to and from the second die. The die may be any of a number of types of electronic components, such as power transistors, memory chips, or others. The stacking of the die saves board space, allowing for further miniaturization or incorporation of additional electronic components.

15 Claims, 7 Drawing Sheets

IMPLANTABLE DEFIBRILLATOR WITH STACKED TRANSISTOR SUBASSEMBLIES

BACKGROUND OF THE INVENTION

1. Field of the Invention

This invention relates generally to implantable cardiac stimulators, and more particularly to the circuit modules encased within cardiac stimulators.

2. Description of the Related Art

The advent of implantable cardiac stimulation systems, such as pacemakers and defibrillators, has brought welcome relief to many patients suffering from various forms of cardiac arrhythmia. Conventional cardiac stimulator systems typically consist of a cardiac stimulator and one or more elongated leads. The cardiac stimulator may be a pacemaker, a defibrillator, a sensing instrument, or some combination thereof. The circuitry, batteries, and other components of the cardiac stimulator are ordinarily encased within a metallic housing commonly referred to as a "can." Most of the electronic components for the cardiac stimulator are mounted on a small circuit board commonly known as a multi-chip module (hereinafter "MCM").

The proximal ends of the leads of the cardiac stimulator system are connected physically and electrically to the cardiac stimulator via a structure commonly known as a header. The distal end of the lead is implanted near the site requiring electrical stimulation or sensing. The leads function to carry electrical signals from the cardiac stimulator to the targeted tissue and signals from the targeted tissue back to the cardiac stimulator.

For most implantable cardiac stimulators, implantation requires an incision in the right or left pectoral region above the areola and formation of a pocket in the subcutaneous tissue by blunt dissection. The leads are then passed into the body to the sites requiring electrical stimulation, usually with the aid of a stylet. The proximal ends of the leads are then connected to the header of the cardiac stimulator and the cardiac stimulator is inserted through the incision and placed in the pocket. The incision is then closed by conventional suturing. The post-operative appearance of the implant area will depend to a large degree on the size of the cardiac stimulator.

The first implantable cardiac stimulators were relatively bulky devices requiring large tissue pockets for implantation. The size of successive generations of implantable cardiac stimulators has diminished dramatically, particularly in the past ten years. Much of this advance in miniaturization is due to advances in the design of semiconductor circuits and fabrication processes.

Size reduction of the internal circuitry of cardiac stimulators has always been an important design goal for engineers. The reasons are at least two-fold. Smaller MCMs can be housed in smaller cans. Smaller cans translate into smaller surgical incisions, smaller subcutaneous pockets, and smoother postoperative skin surfaces. Miniaturization in circuitry also translates into higher device density on the MCM. The result is that more circuitry may be packed into the same or a smaller space. This has to the development of much more sophisticated cardiac stimulators that can perform many different types of useful therapeutic functions, and programmed and reprogrammed to match the patient's condition.

A conventional MCM module consists of a number of electronic devices disposed on one or both sides of a flat insulating substrate. Depending upon the type of cardiac stimulator, the devices may be discreet devices, such as resistors and capacitors, or more highly integrated devices, such as power transistors, microprocessors, telemetry circuits, or induction coils for rechargeable storage devices. These integrated circuits are normally fabricated on a semiconductor chip or die. Many types of electronic devices, such as microprocessors, are commonly disposed in a semiconductor package, such as a PLCC, CERDIP or other type of package that is pin soldered or surface mounted to the MCM substrate. Other devices, such as power transistors, are commonly connected to the MCM substrate as bare die using the well known chip-and-wire technique. In this technique, the bare die are surface mounted to the MCM substrate and bonding wires are connected to the bond pads of the die and to the conductor traces on the substrate by thermal sonic or thermal pressure bonding techniques. Separate space on the MCM substrate must be allotted for each die.

Conventional chip-and-wire processing has certain disadvantages. To begin with, surface mount processing and chip-and-wire processing are generally incompatible. The problem stems from the fact that the solder and solder flux used to mount a surface mount package may short or damage the tiny bonding wires connecting the bonding pads of a bare die to the MCM substrate. One method currently used to alleviate the incompatibility problem involves mounting bare die on one side of the MCM substrate using chip-and-wire processing, and surface mounting other components on the opposite side of the MCM substrate. This method requires complex metallization on both sides of the MCM substrate. In addition, chip-and-wire technology requires separate space on the MCM substrate for each component. This technique limits the potential miniaturization of cardiac stimulators and does not free up space on the MCM substrate that could otherwise be used to incorporate additional useful electronic components into the MCM. Finally, each chip-and-wire mounted component must be separately tested. Such component-by-component electrical testing adds to cost of the overall manufacturing process.

The present invention is directed to overcoming or reducing one or more of the foregoing disadvantages.

SUMMARY OF THE INVENTION

In accordance with one aspect of the present invention, a circuit module for a defibrillator that has a can is provided. The circuit module includes a first substrate dimensioned to fit inside the can, a first die coupled to the first substrate, and a second die. A second substrate is coupled to and disposed between the first die and the second die. The second substrate has a first plurality of conductors to carry electrical signals between the first substrate and the first die and a second plurality of conductors to carry electrical signals between the first substrate and the second die.

In accordance with another aspect of the present invention, a transistor module for a defibrillator that has a circuit module is provided. The transistor module includes a first die that has a first bipolar transistor and a second die that has a second transistor. A substrate is coupled to and disposed between the first die and the second die. The substrate has a first plurality of conductors to carry electrical signals to and from the first transistor, and a second plurality of conductors to carry electrical signals to and from the second transistor.

In accordance with still another aspect of the present invention, an implantable cardiac defibrillator is provided. The implantable cardiac defibrillator includes a can, a storage cell for powering the defibrillator, and a circuit module disposed in the can for controlling the defibrillator. The circuit module has a first substrate, a first die coupled to the first substrate, a second die, and a second substrate coupled to and disposed between the first die and the second die. The second substrate has a first plurality of conductors to carry electrical signals to and from the first die and a second plurality of conductors to carry electrical signals to and from the second die.

In accordance with yet another aspect of the present invention, an implantable cardiac defibrillator is provided. The implantable cardiac defibrillator includes a can, a storage cell for powering the defibrillator, a first substrate disposed in the can, and a transistor module coupled to the first substrate. The transistor module has a first die coupled to the first substrate, a second die, and a second substrate coupled to and disposed between the first die and the second die. The second substrate has a first plurality of conductors to carry electrical signals between the first substrate and the first die and a second plurality of conductors to carry electrical signals between the first substrate and the second die.

In accordance with still another aspect of the present invention, a sub-module for an implantable medical device that has a circuit module is provided. The sub-module includes a substrate that has an upper side and a lower side and a first plurality of conductors coupled to the upper side for carrying electrical signals to and from the circuit module and a second plurality of conductors coupled to the lower side for carrying electrical signals to and from the circuit module. The substrate has a via and a conducting interconnect disposed in the via. A first die is coupled face down to upper side of the substrate and is in electrical connection with the first plurality of conductors and the interconnect. A second die is coupled face down to the lower side of the substrate and is in electrical connection with the second plurality of conductors and the interconnect.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
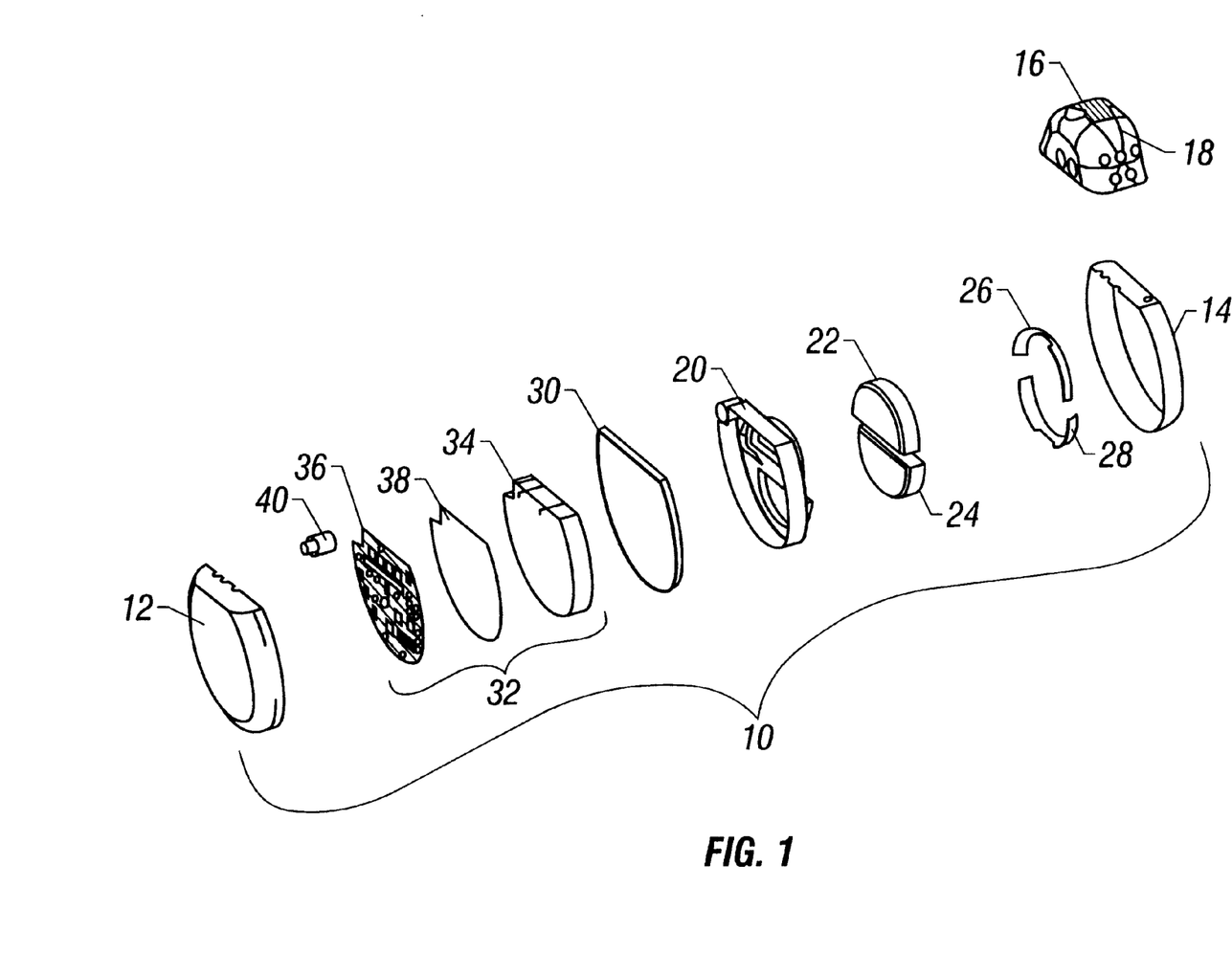
FIG. 1 is an exploded pictorial view of an exemplary embodiment of an implantable defibrillator in accordance with the present invention.

In the drawings described below, reference numerals are generally repeated where identical elements appear in more than one figure. Turning now to the drawings, and in particular to FIG. 1, there is shown an exemplary cardiac defibrillator 10 illustrated in an exploded pictorial view. The defibrillator 10 includes a titanium can shown divided into two mating halves 12 and 14. When joined, the two halves 12 and 14 are connected to a header 16 that is fabricated from epoxy or molded plastic. The header 16 is provided with one or more ports 18 for receiving the proximal ends of cardiac leads (not shown). A polymeric retainer 20 is provided to hold the various internal components of the defibrillator within the shells 12 and 14.

Two storage cells 22 and 24 based on lithium-silver-vanadium or other chemistries are held by the retainer 20 and a pair of polymeric retaining clips 26 and 28 composed of polypropylene or like materials. A communications coil 30 is wrapped around the retainer 20. The communications coil 30 is preferably prewound on a polyamide backing. An electronics subassembly 32 is held by the retainer 20. The electronics subassembly 30 includes one or more high voltage capacitors 34, a circuit module 36, an insulating spacer 38, and a power transformer 40. The high voltage capacitors 34 and the circuit module 36 are separated by the spacer 38. The circuit module 36 holds substantially all of the electronics for the defibrillator 10. The power transformer 40 is provided to step up the voltage supplied by the storage cells 22 and 24 to a higher voltage for storage on the high voltage capacitors 34.

Figure 2:
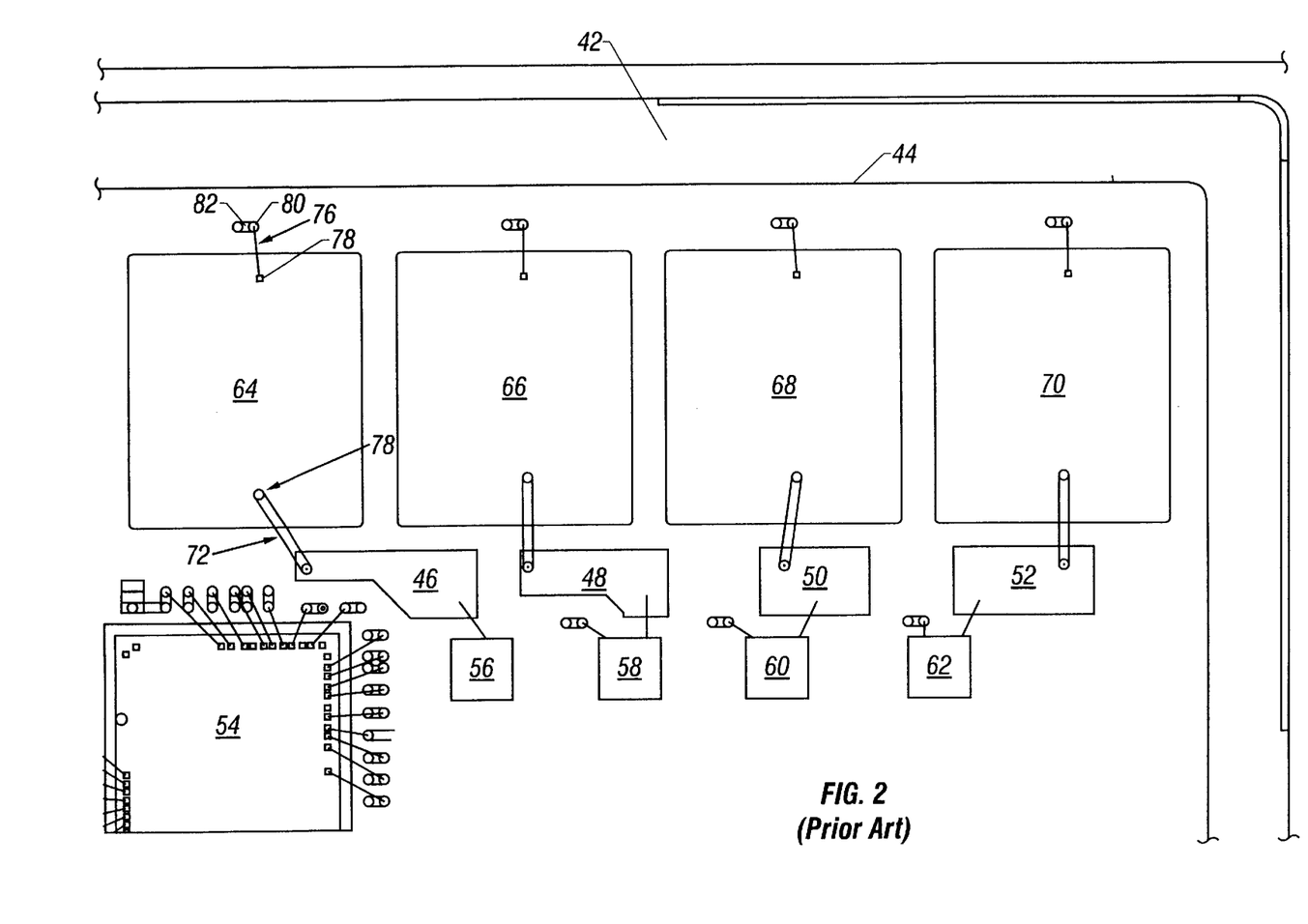
FIG. 2 is a plan view of a portion of a conventional circuit module for a conventional implantable cardiac stimulator.

The detailed structure of a conventional circuit module may be understood by referring now also to FIG. 2, which shows a portion of a conventional circuit module. The portion of a conventional circuit module 42 includes a printed circuit board ("PCB") 44 composed of an insulating ceramic material, such as aluminum oxide or similar materials, or plastic materials, such as polycarbonate plastic or like plastic materials. The PCB 44 includes a number of metallization traces which provide interconnections for various components on the PCB 44. Four of those traces are illustrated at 46, 48, 50, and 52. A microprocessor 54, application specific integrate circuits (hereinafter "ASIC") 56, 58, 60, and 62, and four power transistors 64, 66, 68 and 70 are mounted on the PCB 44. The power transistors 64, 66, 68 and 70 are mounted on the PCB 44 in a row. Each of the power transistors 64, 66, 68 and 70 consists of an individual die occupying a separate area on the PCB 44. Electrical connection between a given power transistor, such as the transistor 64, and its corresponding metal trace 46 is established by a bonding wire 72 that is connected at one end to a bond pad 74 on the die 64 and at the other end to the trace 46 via thermal sonic, thermal pressure, or like techniques. Electrical connection between the die 64 and other traces on the PCB 44 is established by an additional bonding wire 76 that is soldered at one end to another bond pad 78 on the die 64 and at the other end to a trace 80 that projects down into a via 82 that leads to the reverse side of the PCB 44. The interconnection scheme illustrated for the die 64 is commonly referred to as chip-and-wire mounting and is used to connect the other devices shown in FIG. 2.

Figure 3:
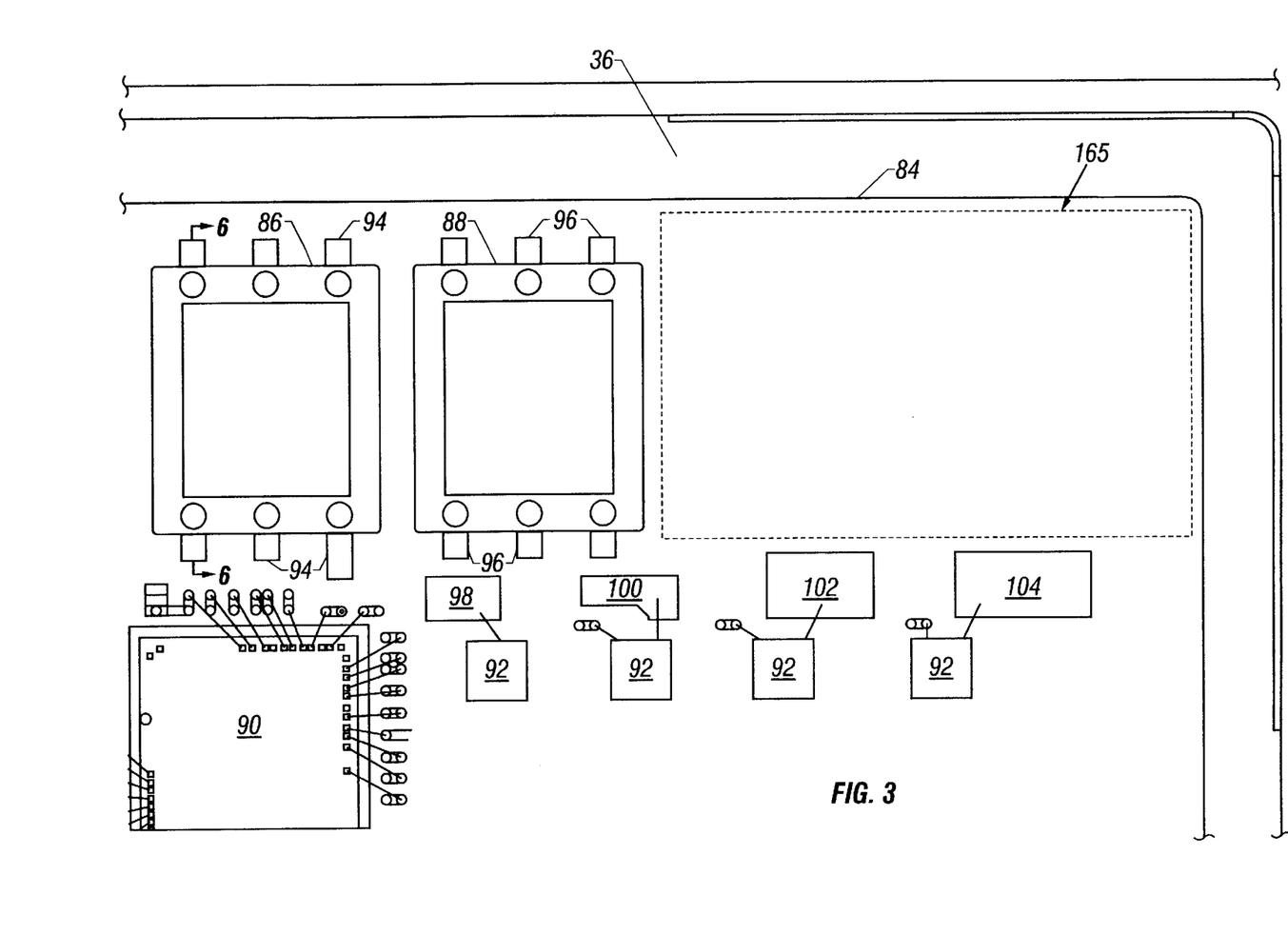
FIG. 3 is a plan view of a portion of a circuit module showing a transistor module for an implantable cardiac defibrillator in accordance with the present invention.

The detailed structure of a new circuit module 36 in accordance with the present invention in accordance with the present invention may be understood by referring now to FIG. 3. The circuit module 36 includes a substrate 84, which may be a PCB or other type of substrate composed of polycarbonate plastic or a ceramic material. Two sub or transistor modules 86 and 88 are mounted to the substrate 84 for providing charging power to the capacitors depicted in FIG. 1. A microprocessor 90 for controlling the defibrillator, and four ASICs 92 are also shown mounted on the substrate 84. The person of ordinary skill in the art should appreciate that the depictions of the microprocessor 90 and the ASICs 92 are illustrative, as the type, number and placement and functionality of particular components is a matter of design discretion. The substrate 84 includes conductor traces 94 and 96 that interconnect various components of the transistor modules 86 and 88. Conductor traces 98, 100, 102 and 104 are provided to connect the ASICs 92 to other portions of the circuit module 36.

Figure 4:
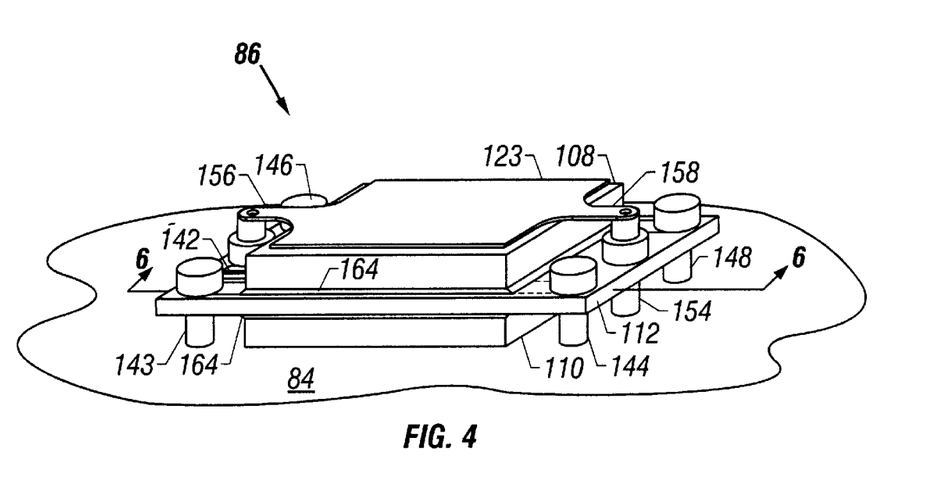
FIG. 4 is a pictorial view of the transistor module of FIG. 3 in accordance with the present invention.
Figure 5:
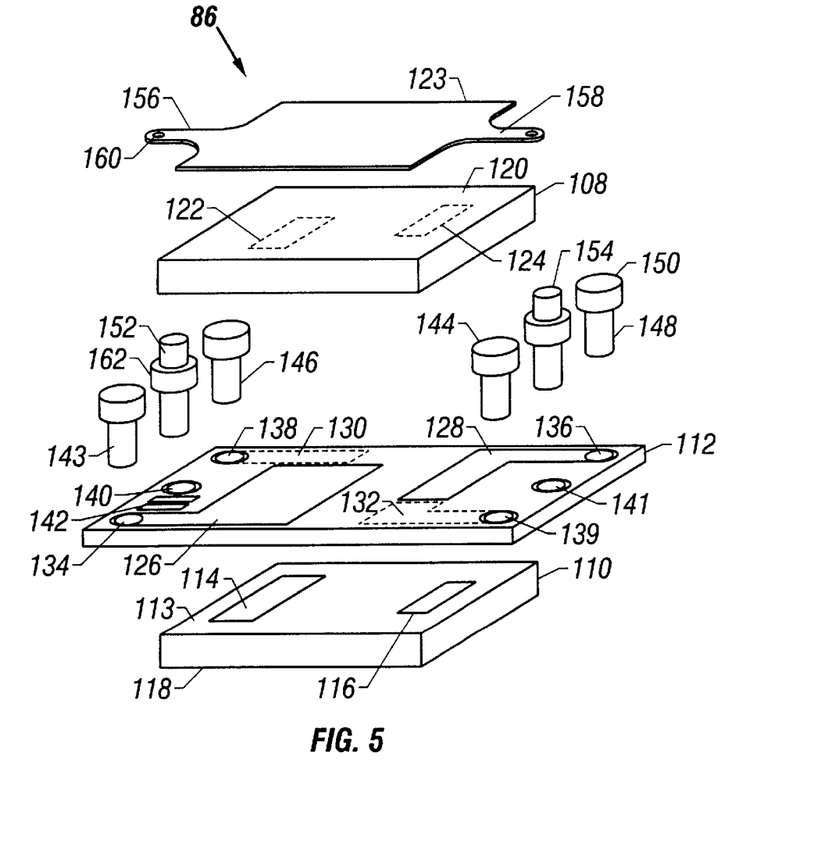
FIG. 5 is an exploded pictorial view of the transistor module of FIG. 4.

The detailed structure of the transistor modules 86 and 88 may be understood by referring now to FIGS. 4 and 5, which are, respectively, assembled and exploded pictorial views of the transistor module 86. The description of the structure and function of the transistor module 86 is also illustrative of the structure and function of the transistor module 88. The transistor module 86 includes two bare die 108 and 110 mounted on a substrate 112. The bare die 108 and 110 are advantageously insulated gate bipolar transistors, but may constitute a variety of types of electrical components, such as, for example, field effect transistors, memory chips, or other integrated circuits. As is well known to those skilled in the art, each die 108 and 110 includes an emitter, a gate, and a collector. The die 110 is mounted to the substrate 112 face-side up with its collector mounted directly on the substrate 84. For simplicity of illustration, the emitter and gate of each die 108 and 110 are not shown and the collector of the die 110 is not visible. The face 113 of the die 110 is provided with a metallic bond pad 114 that is connected to the emitter of the die 110 (not shown), and a bond pad 116 that is connected to the gate of the die 110 (not shown). The underside 118 of the die 110 is taken up by the collector (not visible). The die 108 is structurally identical to the die 110 but is mounted to the substrate 112 face-side down in a flip-chip fashion so that the collector 120 is visible but the bond pads 122 and 124 that are coupled, respectively, to the emitter and the gate (not shown) of the die 108 are shown in phantom. A conductive sheet 123 of gold plated Kovar or similar materials is secured to the collector 120 of the die 108 by well known soldering techniques.

The substrate 112 is designed to electrically insulate the die 108 from the die 110 as well as provide supporting structure for electrical conductors between the substrate 84 and the various bond pads and collectors of the die 108 and 110. In this regard, the substrate 112 is advantageously composed of an insulating ceramic material, such as aluminum oxide or similar materials, or plastic materials, such as polycarbonate plastic or like plastic materials. The substrate 112 is provided with conductive traces 126 and 128 to connect, respectively, with the bond pads 122 and 124, and a corresponding set of conductive traces 130 and 132 disposed on the underside of the substrate (shown in phantom in FIG. 5) to connect, respectively, with the bond pads 114 and 116. The traces 126, 128, 130, and 132 terminate at one end in respective bores 134, 136, 138, and 139 formed in the substrate 112. The traces 126, 128, 130, and 132 are advantageously composed of gold or other suitable solderable conducting materials. Each of the bores 134, 136, 138, and 139 includes some metallization that is contiguous with its respective trace 126, 128, 130, or 132. Two additional bores 140 and 141 are provided in the substrate 112 as will be described in more detail below.

At the time the die 108 and 110 are secured to the substrate 112, it is desirable for the die 108 and 110 to be properly aligned on the substrate 112 so that the bond pads 114, 116, 122, and 124 are in vertical alignment with their respective traces 126, 128, 130, or 132, and so that the edges of the die 108 and 110 do not obstruct the bores 134, 136, 138, and 139. In this regard, an alignment pad 142 is disposed on the upper surface of the substrate 112 to provide an alignment reference for the die 108. An identical alignment pad (not visible) is disposed on the underside of the substrate 112 to provide a reference for the die 110. The alignment pads 142 are located proximate to a known trace to enable quick visual identification of the orientation of all of the traces 126, 128, 130, or 132. The alignment pads 142 may be fabricated from the same materials used to form the traces 126, 128, 130, or 132, or may be punched or otherwise formed into the substrate 112 itself.

To establish electrical connection between the traces 126, 128, 130, and 132 and the substrate 84, conductor pins 143, 144, 146, and 148 are provided, respectively, in the bores 134, 136, 138, and 139 and soldered at their upper ends to their respective trace 126, 128, 130, or 132 and at their lower ends to one of the traces 94 on the substrate 84. Each pin 143, 144, 146, and 148 is provided with a cap 150 that is larger in diameter than the bores 134, 136, 138, and 139. The caps 150 act as stops to prevent the pins 143, 144, 146, and 148 from falling through the bores 134, 136, 138, and 139. The pins 143, 144, 146, and 148 are advantageously composed of gold-plated Kovar or like materials. The solder is advantageously gold-tin eutectic solder or similar solder materials.

Electrical connection between the conducting sheet 123 and the substrate 84 is provided by two conductor pins 152 and 154, which are solder connected, respectively, at their upper ends to tapered projections 156 and 158 in the conducting sheet 123, and which are disposed in the bores 140 and 141 in the substrate 112. Each projection 156 and 158 is provided with a bore 160 that is designed to receive a ball of solder. The pins 152 and 154 are provided with expanded diameter portions 162 that serve the same function as the caps 150 and are fabricated from the same materials used to fashion the pins 143, 144, 146, and 148.

The combination of a given conductor pin, such as 143, and a given trace, such as 126 provides a conductor to carry electrical signals between the substrate 84 and the die 108. Other combinations, such as trace and bonding wire, or other arrangements may be used as well.

Figure 6:
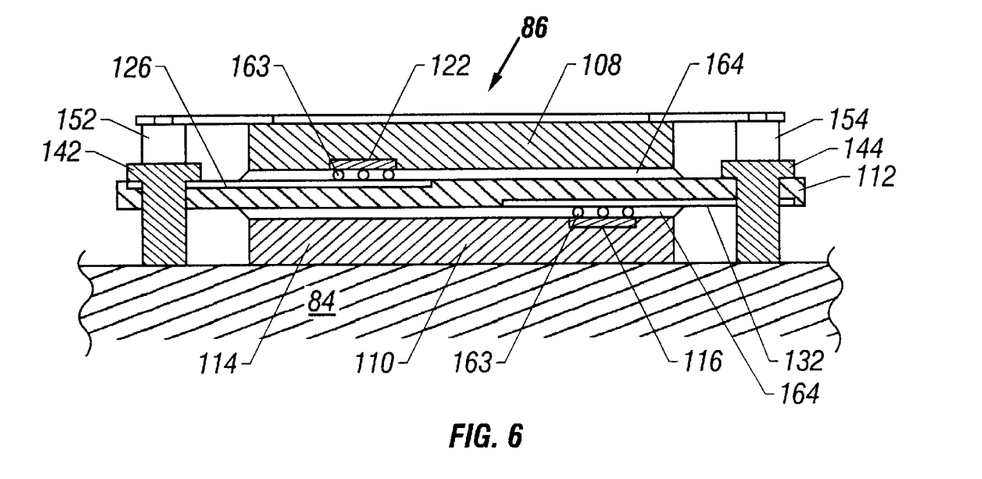
FIG. 6 is a cross-sectional view of FIG. 4 taken at section 6-6.

The detailed structure of the physical and electrical connection between the die 108 and 110 and the substrate 112 may be understood by referring now to FIG. 6. The following description of the connections between the bond pad 122 of the die 108 and the trace 126, and the bond pad 116 of the die 110 and the trace 132 are exemplary of the other connections between the other pads and traces on the die 108 and 110. The bond pads 122 and 116 are connected to the conductor traces 126 and 132 by soldering, and advantageously by bump soldering as evidenced by the presence of the solder bumps 163. A number of well known bump connecting techniques may be used, such as non-melting high temperature bump soldering, completely melting bump soldering, partially melting bump soldering (copper core), as well as other techniques, such as application of a Z-axis conductive polymer material, or similar techniques.

The presence of the solder bumps will leave a gap between the die 108 and 110 and the substrate 112. These gaps are advantageously filled with a polymeric flip-chip underfill material 164 that not only provides a cushion between the substrate 112 and the die 108 and 110, but also provides protection against cracking of the bumps 163 that may result from thermal stresses created by the dissimilar thermal conductivities of the die 108 and 110 and the substrate 112.

An exemplary process flow for assembling the transistor module 86 may be understood by referring now to FIG. 5. It should be understood that the precise order of steps is a matter of design discretion. The substrate 112 is drilled to establish the bores 134, 136, 138, and 139 and the traces 126, 128, 130, and 132 are established thereon. The traces 126, 128, 130, or 132 may be formed by well-known thin film or thick film metallization techniques. The die 108 and 110 are aligned on the substrate 112 via the alignment pads 142 and secured so that the bond pads 114, 116, 122, and 124 of the die 108 and 110 are aligned with and soldered to their respective traces 126, 128, 130, or 132.

The conductor pins 143, 144, 146, and 148 are placed in their respective bores 134, 136, 138, or 139 and soldered into place. The conductive sheet 123 is secured to the collector 120 of the die 108 and soldered to the conductor pins 152 and the 154. The module 86 is then secured to the substrate 84 by soldering so that the collector (not shown) of the die 110 is in contact with one of the traces 94 on the substrate 84.

The advantage of stacking the die 108 and 110 in the transistor modules 86 and 88 may be appreciated by referring again to FIGS. 2 and 3. The two stacked transistors modules 86 and 88 shown FIG. 3 have replaced the four separately mounted and spaced apart transistors 64, 66, 68, and 70 shown in FIG. 2. The dashed box 165 in FIG. 3 shows the area of the substrate 84 that has been saved by the more highly integrated arrangement of the die 108 and 110. The space savings may be translated into a reduction in the size of the substrate 84 and, in turn, the circuit module 36, or may be used to incorporate additional useful electronic components into the circuit module 36. This space savings may be applied to other areas of the circuit module 36 by stacking other types of devices into modules.

Figure 7:
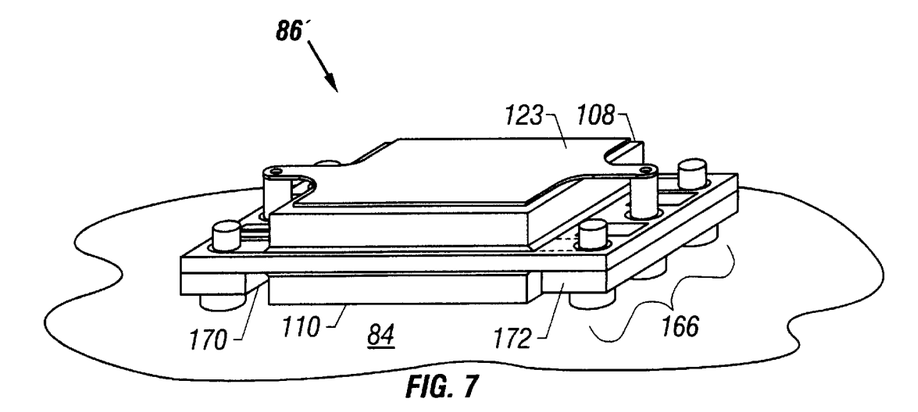
FIG. 7 is a pictorial view of an alternate embodiment of a transistor module in accordance with the present invention.
Figure 8:
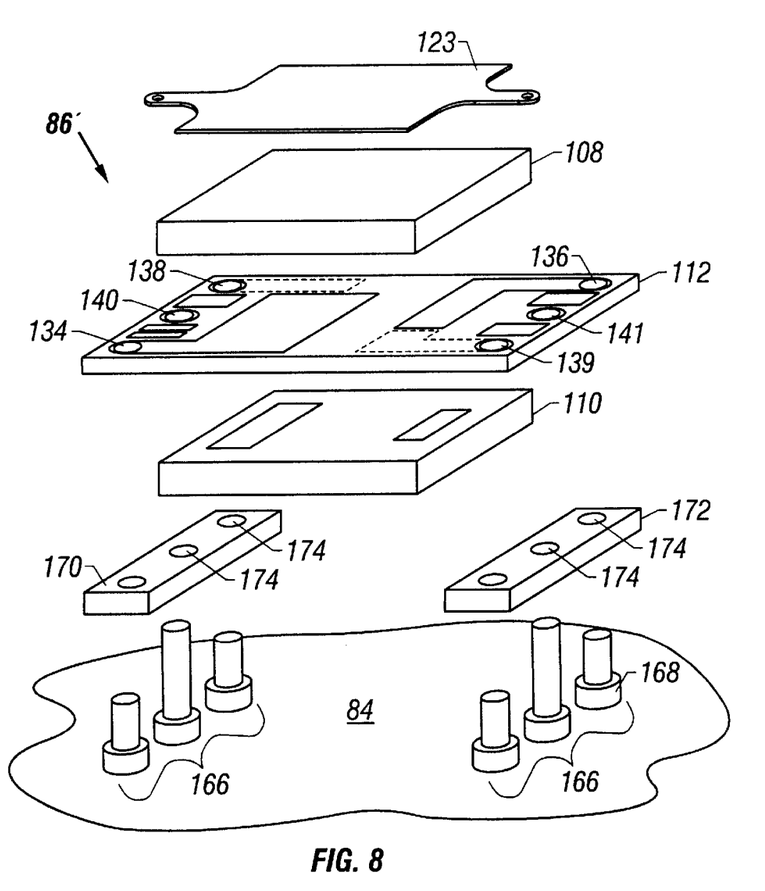
FIG. 8 is an exploded pictorial view of the transistor module of FIG. 7.

FIGS. 7 and 8 depict, respectively, unexploded and exploded pictorials of an alternate embodiment of the transistor module, now designated 86', that is configured to be secured to the substrate 84 by conductive epoxy rather than by soldering. The structure, function, and cooperation of the die 108 and 110, the conductor sheet 123, and the substrate 112 are the same as depicted in FIGS. 3, 4, 5, and 6. However, this embodiment is provided with six conductor pins (all designated 166). The pins 166 are inverted from the orientation of the pins shown in FIGS. 3, 4, 5, and 6 so that the cap 168 of each pin 166 may be secured to the substrate 84 by conductive epoxy or soldering. The larger diameter of the caps 168 relative to the tops of the pins 166 provides a relatively larger surface area to facilitate a stronger bond with the conductive epoxy. To maintain the pins 166 in proper vertical alignment both prior to and after bonding to the substrate 84 and to ensure that the lower surfaces of the caps 168 are approximately horizontally aligned with the lower surface of the die 110, the module 86' may be provided with two rectangular shims 170 and 172. The shims 170 and 172 are dimensioned to be secured to the underside of the substrate 112 on opposite sides of the die 110. The shims 170 and 172 are drilled with bores 174 that align vertically with the bores 134, 136, 138, 139, 140, and 141 in the substrate 112. The shims are advantageously fabricated from the same materials used to make the substrate 112.

An exemplary process flow for assembling the transistor module 86' may be understood by referring now to FIG. 8. It should be understood that the precise order of steps is a matter of design discretion. The steps of preparing the substrate 112 and securing the die 108 and 110 are identical to the process described above. To attach the conductor pins 166, the substrate 112 is flipped over, the shims 170 and 172 are laid on the substrate 112 so that the bores 174 align with the bores 134, 136, 138, 139, 140, and 141, and the conductor pins 166 are inserted and soldered. The module 86' is then secured to the substrate 84 by application of conductive epoxy.

Figure 9:
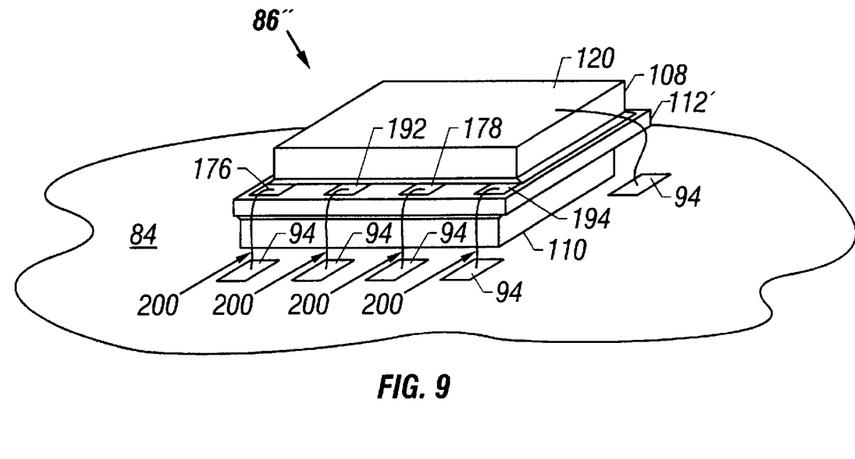
FIG. 9 is a pictorial view of an another alternate embodiment of a transistor module in accordance with the present invention.
Figure 10:
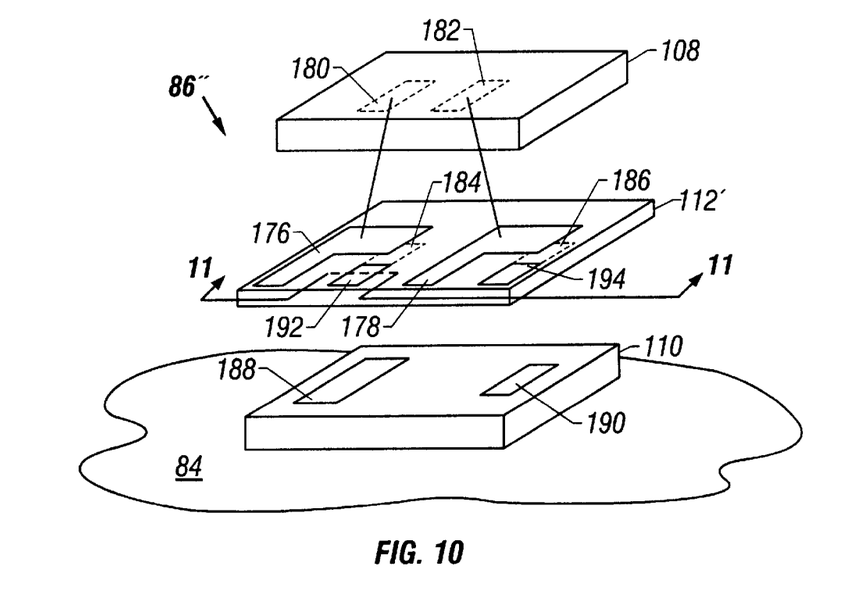
FIG. 10 is an exploded pictorial view of the transistor module of FIG. 9.
Figure 11:
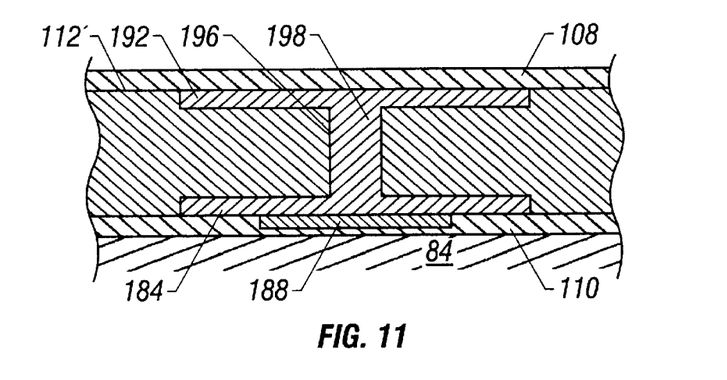
FIG. 11 is a sectional view of FIG. 10 taken at section 11—11.

FIGS. 9 and 10 depict, respectively, unexploded and exploded pictorial views of another alternate embodiment of the transistor module, now designated 86". FIG. 11 depicts a sectional view of FIG. 10 taken at section 11—11. In this embodiment the die 108 and 110 are mounted to the substrate, now designated 112', in a flip-chip orientation as disclosed above. The die 110 may be coupled to the substrate 84 by soldering or conductive epoxy as disclosed above. The upper side of the substrate 112' is provided with metallic conductor traces 176 and 184 for solder connection to bond pads 180 and 182 (shown in phantom) disposed on the underside of the die 108. There is a similar pair of conductor traces 184 and 186 (shown in phantom) and disposed on the underside of the substrate 112' for solder connection to the bond pads 188 and 190. Conductor traces 192 and 194 are provided on the upper side of the substrate 112' and are connected, respectively, to the traces 184 and 186. The connection between the conductor trace 192 and the trace 184 is exemplary of the connection between the trace 194 and the trace 186 and may be understood by referring to FIG. 11. The substrate 112' is provided with a via 196 in which an interconnect 198 is disposed that connects the trace 192 to the trace 184. The interconnect 198 may be integrally metallized with the traces 192 and 184 as shown, or deposited as a separate component by soldering or similar techniques prior to installation of the traces 192 and 184.

In this embodiment, electrical connection between each of the traces 176, 178, 192, and 194, and a corresponding trace 94 on the substrate 84 is accomplished via a bonding wire 200 that is soldered at one end to each trace 176, 178, 192, and 194, and at the other end to a trace 94. Note that one of the bonding wires 200 must be soldered to the collector 120. To ensure that an adequate amount of the traces 176, 178, 192, and 194 are exposed from beneath the die 108 and 110 to facilitate ready attachment of the bonding wires 200, the substrate 112' should be dimensioned to have a slightly larger surface area than the die 108 and 110, and at least one edge of each of the traces 176, 178, 184, and 186 should be disposed near the outer edge of the substrate 112'. The bonding wires 200 are advantageously composed of gold or like conducting materials.

An exemplary process flow for assembling the transistor module 86" may be understood by referring now to FIG. 10. It should be understood that the precise order of steps is a matter of design discretion. The substrate 112' is subjected to metallization and the die 108 and 110 are secured as described above. The module 86' is then secured to the substrate 84 by soldering or application of conductive epoxy and the bonding wires 192 are installed to complete the assembly.

Depending on the types of the electrical devices implemented in the die 108 and 110, it may be desirable not only to interconnect the die 108 and 110 to the substrate 84, but also to connect the die 108 to the die 110. This interconnection between the die 108 and 110 may be readily accomplished by providing the substrate 112' with through-substrate metallization of the type shown in FIG. 11 that interconnect locations on the die 108 directly to locations on the die 110.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims. For example, the invention, has been described herein in the context of a defibrillator. However, the skilled artisan will appreciate that other types of implantable medical devices may benefit from incorporation of the invention therein, such as implantable infusion pumps and implantable neuromuscular stimulators.

What is claimed is:

1. A circuit module for an implantable medical device having a can, comprising:
   a first substrate dimensioned to fit inside the can;
   a first die coupled to the first substrate;
   a second die; and
   a second substrate coupled to and disposed between the first die and the second die, the second substrate having a first plurality of conductors coupled to the first substrate and to the first die to carry electrical signals between first substrate and the first die and a second plurality of conductors coupled to the first substrate and the second die to carry electrical signals between the first substrate and the second die.

2. The circuit module of claim 1, wherein each of the first and second plurality of conductors comprises a conductor trace coupled to a corresponding conductor pin.

3. The circuit module of claim 1, wherein each of the first and second plurality of conductors comprises a conductor trace coupled to a corresponding bonding wire.

4. The circuit module of claim 1, wherein the first die and the second die comprise transistors.

5. The circuit module of claim 4, wherein the transistors comprise insulated gate bipolar transistors.

6. The circuit module of claim 5, wherein at least some of said insulated gate transistors have collectors mounted directly on the second substrate and the second substrate has a conductor layer coupled to said collectors and to one of the second plurality of conductors.

7. An implantable cardiac defibrillator, comprising:
   a can;
   a storage cell for powering the defibrillator; and
   a circuit module disposed in the can for controlling the defibrillator, the circuit module having a first substrate, a first die coupled to the first substrate, a second die, and a second substrate coupled to and disposed between the first die and the second die, the second substrate having a first plurality of conductors to carry electrical signals to and from the first die and a second plurality of conductors to carry electrical signals to and from the second die.

8. The implantable cardiac defibrillator of claim 7, wherein each of the first and second plurality of conductors comprises a conductor trace coupled to a corresponding conductor pin.

9. The implantable cardiac defibrillator of claim 7, wherein the first die and the second die comprise transistors.

10. The implantable cardiac defibrillator of claim 7, wherein the transistors comprise insulated gate bipolar transistors.

11. The implantable cardiac defibrillator of claim 10, wherein the circuit module has a conductor layer coupled to the collector of the second die and to one of the second plurality of conductors.

12. An implantable cardiac defibrillator, comprising:
    a can;
    a storage cell for powering the defibrillator;
    a first substrate disposed in the can for controlling the defibrillator; and
    a transistor module coupled to the first substrate, the transistor module having a first die coupled to the first substrate, a second die, and a second substrate coupled to and disposed between the first die and the second die, the second substrate having a first plurality of conductors to carry electrical signals between the first substrate and the first die and a second plurality of conductors to carry electrical signals between the first substrate and the second die.

13. A sub-module for an implantable medical device having a circuit module, comprising:
    a substrate having an upper side and a lower side and a first plurality of conductors coupled to the upper side for carrying electrical signals to and from the circuit module and a second plurality of conductors coupled to the lower side for carrying electrical signals to and from the circuit module, the substrate having a via and a conducting interconnect disposed in the via;
    a first die coupled face down to the upper side of the substrate and being in electrical connection with the first plurality of conductors and the interconnect; and
    a second die coupled face down to the lower side of the substrate and being in electrical connection with the second plurality of conductors and the interconnect.

14. The sub-module of claim 13, wherein each of the first and second plurality of conductors comprises a conductor trace coupled to a corresponding conductor pin.

15. The sub-module of claim 13, wherein each of the first and second plurality of conductors comprises a conductor trace coupled to a corresponding bonding wire.

* * * * *